(12) United States Patent
Clapp et al.

(10) Patent No.: US 9,636,283 B2
(45) Date of Patent: May 2, 2017

(54) NON-MIGRATING COLORANTS IN MULTI-PHASE PERSONAL CLEANSING COMPOSITIONS

(75) Inventors: Mannie Lee Clapp, Mason, OH (US); Karl Shiqing Wei, Mason, OH (US); Christopher Garrett Anderson, Columbus, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1003 days.

(21) Appl. No.: 13/467,107

(22) Filed: May 9, 2012

(65) Prior Publication Data

US 2012/0220510 A1 Aug. 30, 2012

Related U.S. Application Data

(63) Continuation of application No. 11/304,831, filed on Dec. 15, 2005, now abandoned.

(51) Int. Cl.
*A61K 8/03* (2006.01)
*A61Q 19/10* (2006.01)
*A61K 8/02* (2006.01)

(52) U.S. Cl.
CPC .............. *A61K 8/03* (2013.01); *A61K 8/0295* (2013.01); *A61Q 19/10* (2013.01); *A61K 2800/43* (2013.01)

(58) Field of Classification Search
CPC ........................... A61K 2800/43; A61Q 19/10
See application file for complete search history.

(56) References Cited

U.S. PATENT DOCUMENTS

| | | |
|---|---|---|
| 2,020,454 A | 11/1935 | Bisbee et al. |
| 2,438,091 A | 3/1948 | Lynch |
| 2,528,378 A | 10/1950 | Mannheimer |
| 2,658,072 A | 11/1953 | Kosmin |
| 2,986,271 A | 5/1961 | Forrer |
| 3,455,440 A | 7/1969 | West |
| 3,479,429 A | 11/1969 | Morshauser et al. |
| 3,533,955 A | 10/1970 | Pader et al. |
| 3,542,256 A | 11/1970 | Waterman |
| 3,618,757 A | 11/1971 | Funkhouser |
| 3,800,998 A | 4/1974 | Gask |
| 3,850,365 A | 11/1974 | Dietrich |
| 3,852,475 A | 12/1974 | Tarangul |
| 3,899,076 A | 8/1975 | Florian |
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Barker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,818,575 A | 4/1989 | Hirata et al. |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,912 A | 7/1993 | Herget et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A | 9/1996 | Derian et al. |
| 5,578,299 A | 11/1996 | Starch |
| 5,612,307 A | 3/1997 | Chambers et al. |
| 5,632,420 A | 5/1997 | Lohrman et al. |
| 5,635,171 A | 6/1997 | Nadaud |
| 5,661,189 A | 8/1997 | Grievson et al. |
| 5,687,779 A | 11/1997 | Andersson et al. |
| 5,716,920 A | 2/1998 | Glenn et al. |
| 5,804,538 A | 9/1998 | Wei et al. |
| 5,851,978 A | 12/1998 | Shana'a |
| 5,873,494 A | 2/1999 | Dallas, Jr. |
| 5,891,833 A | 4/1999 | Wei et al. |
| 5,925,603 A | 7/1999 | D'Angelo |
| 5,929,019 A | 7/1999 | Puvvada et al. |

(Continued)

FOREIGN PATENT DOCUMENTS

| | | |
|---|---|---|
| DE | 10340348 | 3/2005 |
| EP | 1 108421 A2 | 6/2001 |
| EP | 1 064918 B1 | 9/2002 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |

(Continued)

OTHER PUBLICATIONS

XP 002332778 "Dove All Day Moisturizing Body Wash" Online URL: http://www.ewg.org/reports/skindeep2/report.php?type=PRODUCT&id=8801874 accessed Feb. 8, 2006 (6 pages).

(Continued)

*Primary Examiner* — Kendra D Carter

(57) ABSTRACT

A multi-phase personal cleansing composition comprising: (a) a structured aqueous cleansing phase comprising a surfactant and water; and (b) at least one additional, non-lamellar aqueous phase; wherein at least one of said structured aqueous cleansing phase and said additional aqueous phase comprises at least one non-migrating colorant, said non-migrating colorant comprising a cLogP value of at least about 2; and wherein said structured aqueous cleansing phase and said additional aqueous phase are packaged in physical contact with one another.

13 Claims, No Drawings

(56) References Cited

U.S. PATENT DOCUMENTS

| | | |
|---|---|---|
| 5,947,335 A | 9/1999 | Milio et al. |
| 5,952,286 A | 9/1999 | Puvvada et al. |
| 5,954,213 A | 9/1999 | Gerhart et al. |
| 5,965,500 A | 10/1999 | Puvvada |
| 5,965,501 A | 10/1999 | Rattinger et al. |
| 5,972,361 A | 10/1999 | Fowler et al. |
| D426,158 S | 6/2000 | Flurer et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 | 2/2001 | Glenn, Jr. |
| D438,460 S | 3/2001 | Hammond |
| D439,165 S | 3/2001 | Erckelbout et al. |
| 6,213,166 B1 | 4/2001 | Thibiant et al. |
| D441,645 S | 5/2001 | Longhurst |
| 6,232,496 B1 | 5/2001 | Carr et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |
| 6,340,723 B1 | 1/2002 | Nita et al. |
| D455,655 S | 4/2002 | Bunce |
| 6,367,519 B2 | 4/2002 | Thibiant et al. |
| 6,383,999 B1 | 5/2002 | Coyle et al. |
| 6,385,992 B1 | 5/2002 | Flore, Jr. |
| 6,394,323 B2 | 5/2002 | McClean et al. |
| 6,419,783 B1 | 7/2002 | Rainey et al. |
| 6,426,326 B1 | 7/2002 | Mitra et al. |
| 6,429,177 B1 | 8/2002 | Williams et al. |
| 6,495,498 B2 | 12/2002 | Niemiec et al. |
| 6,506,391 B1 | 1/2003 | Biatry |
| 6,516,838 B2 | 2/2003 | Thibiant et al. |
| 6,517,939 B1 | 2/2003 | Moini et al. |
| 6,521,216 B1 | 2/2003 | Glandorf et al. |
| 6,534,456 B2 | 3/2003 | Hayward et al. |
| 6,534,458 B1 | 3/2003 | Kakizawa et al. |
| 6,547,063 B1 | 4/2003 | Zaveri et al. |
| 6,555,509 B2 | 4/2003 | Abbas et al. |
| 6,564,978 B1 | 5/2003 | Safian et al. |
| 6,574,985 B2 | 6/2003 | Fiore, Jr. |
| 6,589,509 B2 | 7/2003 | Keller et al. |
| 6,652,134 B2 | 11/2003 | Lloyd |
| 6,673,755 B2 | 1/2004 | Wei et al. |
| D486,395 S | 2/2004 | Lovell et al. |
| D486,398 S | 2/2004 | Lovell et al. |
| 6,691,394 B1 | 2/2004 | McClean |
| 6,695,510 B1 | 2/2004 | Look et al. |
| 6,780,826 B2 | 8/2004 | Zhang et al. |
| 6,869,923 B1 | 3/2005 | Cunningham et al. |
| 6,903,057 B1 | 6/2005 | Tsaur |
| 6,906,016 B1 | 6/2005 | Tsaur |
| 6,924,256 B2 | 8/2005 | Massaro et al. |
| 7,143,893 B2 | 12/2006 | Kelly |
| 7,144,542 B2 | 12/2006 | Holzer et al. |
| 7,229,486 B2 | 6/2007 | Wiersema et al. |
| 7,273,837 B2 | 9/2007 | Boutique et al. |
| 7,511,003 B2 | 3/2009 | Focht et al. |
| 7,524,807 B2 | 4/2009 | Clapp et al. |
| 7,537,819 B2 | 5/2009 | Hendricks |
| 7,666,825 B2 | 2/2010 | Wagner et al. |
| 2001/0035230 A1 | 11/2001 | Thibiant et al. |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2002/0032147 A1 | 3/2002 | Foley et al. |
| 2002/0085987 A1 | 7/2002 | Brown et al. |
| 2002/0160026 A1 | 10/2002 | Frechet et al. |
| 2003/0053974 A1 | 3/2003 | Shefer et al. |
| 2003/0152540 A1 | 8/2003 | Putman et al. |
| 2003/0161852 A1 | 8/2003 | Miller et al. |
| 2003/0180246 A1 | 9/2003 | Frantz et al. |
| 2003/0222100 A1 | 12/2003 | Husband et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0091445 A1 | 5/2004 | Dykstra et al. |
| 2004/0092414 A1 | 5/2004 | Clapp et al. |
| 2004/0092415 A1 | 5/2004 | Focht et al. |
| 2004/0105827 A1 | 6/2004 | Grimm et al. |
| 2004/0146475 A1 | 7/2004 | Peffly et al. |
| 2004/0158940 A1 | 8/2004 | Wells et al. |
| 2004/0180020 A1 | 9/2004 | Manelski et al. |
| 2004/0219119 A1 | 11/2004 | Wei et al. |
| 2004/0223929 A1 | 11/2004 | Clapp et al. |
| 2004/0223991 A1 | 11/2004 | Wei et al. |
| 2004/0223993 A1 | 11/2004 | Clapp et al. |
| 2004/0232023 A1 | 11/2004 | Bansal et al. |
| 2004/0235693 A1 | 11/2004 | Wei et al. |
| 2004/0242706 A1 | 12/2004 | Wiersema et al. |
| 2004/0248748 A1 | 12/2004 | Wei et al. |
| 2004/0248749 A1 | 12/2004 | Mitra et al. |
| 2005/0003975 A1 | 1/2005 | Browne et al. |
| 2005/0020468 A1 | 1/2005 | Frantz et al. |
| 2005/0043208 A1 | 2/2005 | Bettiol et al. |
| 2005/0096252 A1 | 5/2005 | Dubois et al. |
| 2005/0100570 A1 | 5/2005 | Wei et al. |
| 2005/0139574 A1 | 6/2005 | Simone et al. |
| 2005/0143269 A1 | 6/2005 | Wei et al. |
| 2005/0153852 A1 | 7/2005 | Evans et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0249758 A1 | 11/2005 | Di Puccio Pagano |
| 2005/0269372 A1 | 12/2005 | Smith |
| 2005/0276768 A1 | 12/2005 | Wei et al. |
| 2006/0002880 A1 | 1/2006 | Peffly et al. |
| 2007/0141001 A1 | 6/2007 | Clapp et al. |
| 2011/0009302 A1 | 1/2011 | Soffin et al. |
| 2011/0117225 A1 | 5/2011 | Wei et al. |

FOREIGN PATENT DOCUMENTS

| | | |
|---|---|---|
| WO | WO 99/38489 A1 | 8/1999 |
| WO | WO 99/38491 A1 | 8/1999 |
| WO | WO 99/62477 A1 | 12/1999 |
| WO | WO 00/75240 A1 | 12/2000 |
| WO | WO 01/01931 A1 | 1/2001 |
| WO | WO 01/25389 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/083031 A1 | 10/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2004/100919 A1 | 11/2004 |
| WO | WO 2005/048959 A1 | 6/2005 |
| WO | WO 2005/065638 A1 | 7/2005 |
| WO | WO 2005/067875 A1 | 7/2005 |
| WO | WO 2005/123031 A1 | 12/2005 |
| WO | WO 2006/093742 A1 | 9/2006 |
| WO | WO 2006/102113 A2 | 9/2006 |

OTHER PUBLICATIONS

Household Products Database, Brand Information, "Olay Daily Renewal Moisturizing Body Wash, Calming,"[Online] URL: http://householdproducts.nlm.nih.gov/cgi-bin/household/brands?tbl=brands&id=16003084, accessed Feb. 8, 2006 (2 pages).

International Search Report, PCT/IB2006/054877, dated May 30, 2007 (5 pages).

C.D. Vaughan, "Solubility, Effects in Product, in Package, Penetration and Preservation," Cosmetic and Toiletries, vol. 103, Oct. 1988.

C.J. van Oss, "Coacervation, Complex-Coacervation and Flocculation," J. Disperion Science and Technology, vol. 9 (5,6), 1988-89, p. 561-657.

Crank, Mathematics of Duffusion, $2^{nd}$ Edition, p. 63.

(56) References Cited

OTHER PUBLICATIONS

CTFA International Cosmetic Ingredient Dictionary, Fourth Edition, 1991, pp. 12 and 80.
D. J. Burgess, "Practical Analysis of Complex Coacervate Systems," J. of Colloid anti Interface Science, vol. 140, No. 1, Nov. 1990, pp. 227-238.
J. Caelles et al., "Anionic and Cationic Compounds in Mixed Systems," Cosmetics & Toiletries, vol. 106, Apr. 1991, pp. 49-54.
KOBO Brochure, "Treated Pigments" (May 2000).

NON-MIGRATING COLORANTS IN MULTI-PHASE PERSONAL CLEANSING COMPOSITIONS

CROSS REFERENCE TO RELATED APPLICATION

This case is a continuation of U.S. application Ser. No. 11/304,831 filed on Dec. 15, 2005, now abandoned the entirety of which is incorporated herein by reference.

FIELD OF THE INVENTION

The present invention relates to multi-phase personal cleansing compositions comprising at least one structured aqueous cleansing phase and at least one additional, non-lamellar aqueous phase wherein at least one of the phases comprises at least one non-migrating colorant comprising a cLogP value of at least about 2 and wherein the two phases are packaged in physical contact with one another while remaining stable over time.

BACKGROUND OF THE INVENTION

The ability to place a cleansing phase in physical contact with a structured aqueous phase and maintain stability for any period of time has proven to be a problem. The physical contact of a structured aqueous phase and a cleansing phase creates a situation where they are thermodynamically unstable.

One attempt at providing a stable, structured aqueous phase and cleansing phase within a personal cleansing product would be the use of dual-chamber packaging. These packages comprise separate cleansing compositions and structured aqueous compositions, and allow for the co-dispensing of the two in a single or dual stream. The separate structured aqueous composition and cleansing compositions thus remain physically separate and stable during prolonged storage and just prior to application, but then mix during or after dispensing to provide conditioning and cleansing benefits from a physically stable system. Although such dual-chamber delivery systems provide improved cleansing benefits versus conventional systems, it is often difficult to achieve consistent and uniform performance because of the uneven dispensing ratio between the cleansing phase and the structured aqueous phase. Additionally, these packaging systems add considerable cost to the finished product.

Another attempt at providing a cleansing and moisturizing benefit composition has been to formulate and package such compositions as disclosed in U.S. Pat. No. 6,534,456 issued to Hayward et al., on Mar. 18, 2003 describing extrudable multi-phase compositions comprising a lamellar phase and an isotropic phase. These exemplified compositions, however, contain water soluble colorants which tend to migrate from one phase to the other. The colorant can be a meaningful aspect of the product to the consumer, connoting both benefit and performance. For a multi-phase system, the colorant can serve to distinguish the two phases from each other. Traditionally, water soluble colorants, i.e. dyes, have been used to color cleansing systems. It has, however, been found that when the compositions of the two phases are chemically distinct, as described herein, color migration of certain commonly used colorants will serve to render multi-phase compositions less visibly distinct which, may decrease their appeal. Stability is integral in such application and thus, there still remains a need for a stable personal cleansing composition that provides cleansing and skin benefits patterned in physical contact within the same package.

SUMMARY OF THE INVENTION

The present invention relates to a multi-phase personal cleansing compositions comprising a structured aqueous cleansing phase and at least one aqueous phase wherein at least one phase comprises a non-migrating colorant. The phases are packaged in physical contact with one another. It has been found that the use of a non-migrating colorant comprising a cLogP value of at least about 2 provides improved color stability within the product by preventing migration of the colorant between the phases.

Specifically, the present invention is directed to a multi-phase personal cleansing composition comprising: (a) a structured aqueous cleansing phase comprising a surfactant and water; and (b) at least one additional aqueous phase; wherein at least one of said structured aqueous cleansing phase and said additional aqueous phase comprises at least one non-migrating colorant, said non-migrating colorant comprising a cLogP value of at least about 2; and wherein said structured aqueous cleansing phase and said additional phase are packaged in physical contact with one another.

The present invention is also directed to a multi-phase personal cleansing composition comprising a) a structured aqueous cleansing phase comprising a surfactant and water; and b) at least one additional aqueous phase; wherein at least one of said structured aqueous cleansing phase and said additional aqueous phase comprises at least one non-migrating colorant, said non-migrating colorant having a cLogP value of at least about 2 and said non-migrating colorant being free of titanium dioxide; and wherein said structured aqueous cleansing phase and said additional phase are packaged in physical contact with one another.

DETAILED DESCRIPTION OF THE INVENTION

The multi-phase personal cleansing compositions of the present invention may comprise at least one structured aqueous cleansing phase and at least one additional aqueous phase, which may be a non-lamellar aqueous phase wherein at least one of the phases comprises at least one non-migrating colorant comprising a cLogP value of at least about 2 and wherein the two phases are packaged in physical contact with one another while improving color stability within the product by preventing migration of the colorant between the phases. While not necessary that the additional aqueous phase be non-lamellar, it is preferred that if the additional aqueous phase is a lamellar phase, the additional aqueous phase should also be free of titanium dioxide.

The compositions of the present invention further provide superior aesthetics via the multi-phased appearance and improved skin feel during and after application. It has been found that such compositions can be formulated into two separate hydrophilic phases in physical contact without compromising product performance and stability.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. Except where specific examples of actual measured values are presented, numerical values referred to herein should be considered to be qualified by the word "about".

All molecular weights as used herein are weight average molecular weights expressed as grams/mole, unless otherwise specified.

As used herein, "comprising" means that other steps and other ingredients which do not affect the end result can be added. This term encompasses the terms "consisting of" and "consisting essentially of". The compositions and methods/processes of the present invention can comprise, consist of, or consist essentially of the essential elements and limitations of the invention described herein, as well as any of the additional or optional ingredients, components, steps, or limitations described herein useful in personal cleansing compositions intended for topical application to the hair or skin.

By the term "multi-phased" or "multi-phase", it is meant that the structured aqueous cleansing phase and the additional aqueous phase herein occupy separate but distinct physical spaces inside the package in which they are stored, but are in direct contact with one another (i.e., they are not separated by a barrier and they are not emulsified or mixed to any significant degree). In the present invention, the "multi-phase" personal cleansing compositions comprising structured aqueous cleansing phase and at least one additional aqueous phase are present within the container as a visually distinct pattern. The pattern results from the mixing or homogenization of the "multi-phased" composition. The patterns include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. The pattern may be striped and may be relatively uniform and even across the dimension of the package. Alternatively, the striped pattern may be uneven, i.e. wavy, or may be non-uniform in dimension. The striped pattern does not need to necessarily extend across the entire dimension of the package. The size of the stripes is at least about 0.1 mm in width and 10 mm in length, preferably at least about 1 mm in width and at least 20 mm in length. The phases can form various geometric shapes, be various different colors, or include glitter or pearlescence.

The term "ambient conditions" as used herein, refers to surrounding conditions at one (1) atmosphere of pressure, 50% relative humidity, and 25° C.

The term "stable" as used herein, unless otherwise specified, refers to compositions that maintain at least two "separate" phases when sitting in physical contact at ambient conditions for a period of at least about 180 days. By "separate", it is meant that there is substantially no mixing of the phases that are observable to the naked eye prior to dispensing of the composition.

The term "personal cleansing composition" as used herein, refers to compositions intended for topical application to the skin or hair.

The term "phases" as used herein, refers to a region of a composition having one average composition, as distinct from another region having a different average composition, wherein the regions are visible to the naked eye. This would not preclude the distinct regions from comprising two similar phases where one phase could comprise pigments, dyes, particles, and various optional ingredients, hence a region of a different average composition.

The phrase "substantially free of" as used herein, means that the composition comprises less than about 3%, less than about 1%, less than about 0.5%, less than about 0.25%, or less than about 0.1%, by weight of the composition, of the stated ingredient.

The phrase "UV stable" as used herein, means stable to UV light exposure. For example, exposure of a composition in a transparent or translucent package to UV light in a Fadometer which utilizes a water cooled xenon lamp to simulate sunlight exposure does not significantly fade the color of the product as determined by a side by side comparison of before and after exposure to 6 hours of light (simulating 30 days sunlight), which can also be determined by having a low delta Ecmc of the colored phase (e.g., delta E may be less than 5, less than 4, less than 3, or less than 2 for a 0.012% colorant slurry in a 60% petrolatum, 39.88% Hydrobrite 1000™ mineral oil mixture).

Product Form

The personal cleansing compositions of the present invention are typically in the form of a liquid. The term "liquid" as used herein means that the composition is generally flowable to some degree. "Liquids", therefore, may include liquid, semi-liquid, cream, lotion or gel compositions intended for topical application to skin. The compositions may exhibit a viscosity of equal to or greater than about 3,000 (centipoise, hereinafter "cps"), equal to or greater than about 5,000 cps, equal to or greater than about 10,000 cps or equal to or greater than about 20,000 cps and no more than about 1,000,000 cps, no more than about 500,000 cps, no more than about 300,000 cps, or no more than about 200,000 cps as measured by the Viscosity Method described hereinafter. Additionally, the ratio of the structured aqueous cleansing phase to the additional aqueous phase may be no more than about 99:1, no more than about 50:1, no more than about 30:1, no more than about 10:1, or no more than about 1:1. The ratio of the structured aqueous cleansing phase to the additional aqueous phase may be at least about 1:99, at least about 1:50, at least about 1:30, at least about 1:10, or at least about 1:1.

The present invention comprises a multi-phased personal cleansing composition wherein the composition has at least two visually distinct phases such that at least one phase is visually distinct from a second phase. The visually distinct phases are packaged in physical contact with one another and are stable.

The product forms contemplated for purposes of defining the compositions and methods of the present invention are rinse-off formulations by which it is meant that the product is applied topically to the skin or hair and then subsequently (i.e., within minutes) rinsed away with water, or otherwise wiped off using a substrate or other suitable removal means.

Structured Aqueous Cleansing Phase

The structured aqueous cleansing phase of the composition of the present invention comprises a structurant, a surfactant and water. The structured aqueous cleansing phase may be structured by the formation of an ordered surfactant phase, such as a lamellar, hexagonal or cubic phase, or the phase may be isotropic and structured by a polymer network. When structured by an ordered surfactant phase, the cleansing phase may also contain polymer for additional structuring.

The structured aqueous cleansing phase may have a lather volume of at least about 500 mL, at least about 700 mL, at least about 1000 mL, or at least about 1250 mL when measured by the lather volume test described herein.

Structurant

The structured aqueous cleansing phase of the present invention may comprise from at least about 0.1%, or from at least about 0.5% and no more than about 30%, no more than about 20%, no more than about 10%, or no more than about 5%, by weight of the structured aqueous phase, of a structurant. The structurant can be used to structure either the water or the surfactant of the structured aqueous cleansing phase. Non-limiting examples of inorganic water structurants for use in the personal cleansing composition of the present invention include silicas, clays such as a synthetic silicates (Laponite XLG™ and Laponite XLS™ from Southern Clay), or mixtures thereof. Non-limiting examples of charged polymeric water structurants for use in the personal cleansing composition include Acrylates/Vinyl Isodecanoate Crosspolymer (Stabylen 30™ from 3V), Acrylates/Vinyl neodecanoate Crosspolymer (Aculyn 38™ from Rohm and Haas) Acrylates/C10-30 Alkyl Acrylate Crosspolymer (Pemulen TR1™ and TR2™), Carbomers, Ammonium Acryloyldimethyltaurate/VP Copolymer (Aristoflex AVC™ from Clariant), Ammonium Acryloyldimethyltaurate/Beheneth-25 Methacrylate Crosspolymer (Aristoflex HMB™ from Clariant), Acrylates/Ceteth-20 Itaconate Copolymer (Structure 3001™ from National Starch), Polyacrylamide (Sepigel 305™ from SEPPIC), or mixtures thereof. Non-limiting examples of water soluble polymeric structurants for use in the personal cleansing composition include cellulosic gel, hydroxypropyl starch phosphate (Structure XL™ from National Starch), polyvinyl alcohol, or mixtures thereof. Non-limiting examples of associative water structurants for use in the personal cleansing composition include synthetic and natural gums and thickeners such as xanthan gum (Ketrol CG-T™ from CP Kelco), succinoglycan (Rheozan™ from Rhodia, gellum gum, pectin, alginates, starches including pregelatinized starches, modified starches, or mixtures thereof.

The structured aqueous cleansing phase of the present invention may comprise from about 0.1%, from about 0.5%, or from about 1% to about 10%, to about 6%, or to about 5% by wt., of a lamellar structurant, which functions in the compositions to form a lamellar phase. It is believed the lamellar phase enhances the interfacial stability between the structured aqueous cleansing phase and the additional aqueous phase of the present compositions. The lamellar phase may have a viscosity in the range of at least about 10,000 cps, at least about 20,000 cps, at least about 30,000 cps, or at least about 40,000 cps.

Suitable lamellar structurants include, but are not limited to, fatty acids or ester derivatives thereof, fatty alcohols, ethoxylated fatty alcohol, trihydroxystearin (available from Rheox, Inc. under the trade name THIXCIN® R), or polymethyacrylamidopropyl trimonium chloride (available from Rhodia under the trade name POLYCARE® 133). If the lamellar structurant is a fatty acid, or an ester of fatty acid, the hydrocarbon backbone can be straight chained or branched. Preferably, the lamellar structurant is selected from lauric acid, fatty alcohols, ethoxylated fatty alcohols, or trihydroxystearin.

Surfactant

The structured aqueous cleansing phase of the present invention comprises a cleansing surfactant suitable for application to the skin or hair. Suitable surfactants for use herein include any known or otherwise effective cleansing surfactant which are suitable for application to the skin, and which are otherwise compatible with the other essential ingredients in the structured aqueous cleansing phase of the composition. These cleansing surfactants include anionic, nonionic, cationic, zwitterionic or amphoteric surfactants, or combinations thereof. Suitable surfactants are described in *McCutcheon's, Emulsifiers and Detergents,* 1989 *Annual,* published by M. C. Publishing Co., and in U.S. Pat. No. 3,929,678.

The structured aqueous cleansing phase of the personal care compositions may comprise a cleansing surfactant at concentrations ranging from about 1%, from about 4%, or from about 5% to about 90%, to about 50%, or to about 30%, by weight of the structured aqueous cleansing phase. The pH range of the structured aqueous cleansing phase may be from about 5 to about 8 or to about 6.

Anionic surfactants suitable for use as cleansing surfactants in the structured aqueous cleansing phase of the present compositions include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, wherein x is about 1 to about 10, and M is a water-soluble cation such as ammonium, sodium, potassium, or triethanolamine. The alkyl ether sulfates are typically made as condensation products of ethylene oxide and monohydric alcohols having from about 8 to about 24 carbon atoms. R may have from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil may be used. Such alcohols may be reacted with about 1 or about 3 to about 10 or about 5 molar proportions of ethylene oxide. The resulting mixture of molecular species may have, for example, an average of 3 moles of ethylene oxide per mole of alcohol, is sulfated and neutralized.

Specific examples of alkyl ether sulfates which may be used in the structured aqueous cleansing phase are sodium and ammonium salts of coconut alkyl triethylene glycol ether sulfate; tallow alkyl triethylene glycol ether sulfate, and tallow alkyl hexaoxyethylene sulfate. Suitable alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1—SO_3-M]$, wherein $R^1$ is chosen from the group consisting of a straight or branched chain, saturated aliphatic hydrocarbon radical having from about 8 to about 24, or about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Suitable anionic surfactants for use in the structured aqueous cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, may be employed in some embodiments. Mixtures of anionic surfactants can also be used in some embodiments.

Other surfactants from the classes of amphoteric, zwitterionic surfactant, cationic surfactant, and/or nonionic surfactant can be incorporated in structured aqueous cleansing phase of the compositions.

Amphoteric surfactants suitable for use as cleansing surfactant in the structured aqueous cleansing phase of the present compositions include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use as cleansing surfactant in the structured aqueous cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

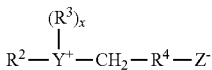

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the structured aqueous cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gammacarboxypropyl betaine, and lauryl bis-(2-hydroxypropyl) alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl)sulfopropyl betaine and the like; amidobetaines and amidosulfobetaines, wherein the $RCONH(CH_2)_3$ radical is attached to the nitrogen atom of the betaine are also useful in the present compositions.

Amphoacetates and diamphoacetates can also be used. Suitable amphoacetates have the formula:

and suitable diamphoacetate have the formula:

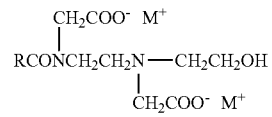

wherein R is an aliphatic group of 8 to 18 carbon atoms; and M is a cation such as sodium, potassium, ammonium, or substituted ammonium. Non-limiting examples of suitable amphoacetates and diamphoacetates include sodium lauroamphoacetate, sodium cocoamphoactetate, disodium lauroamphoacetate, and disodium cocodiamphoacetate.

Cationic surfactants can also be used in the structured aqueous cleansing phase, but are generally less preferred, and thus, may represent less than about 5%, by weight of the structured aqueous cleansing phase.

Suitable nonionic surfactants for use in structured aqueous cleansing phase include condensation products of alkylene oxide groups (hydrophilic in nature) with an organic hydrophobic compound, which may be aliphatic or alkyl aromatic in nature.

Water

The structured aqueous cleansing phase of the present invention may comprise from about 30% to about 99%, by weight of the structured aqueous cleansing phase, of water. Particularly, the structured aqueous cleansing phase generally comprises more than about 50%, more than about 60%, more than about 70%, or more than about 80%, by weight of structured aqueous cleansing phase, of water.

The structured aqueous cleansing phase will typically have a pH of from about 5 or from about 6 to about 8 or to about 7. The structured aqueous cleansing phase can optionally comprise a pH regulator to facilitate the proper pH range. The pH of the structured aqueous cleansing phase may be within +/−0.25 pH units of the additional aqueous phase.

Additional Aqueous Phase

The personal cleansing compositions of the present invention comprise an additional aqueous phase. The aqueous phase may contain between 0% and 30% surfactant. Examples of surfactant containing aqueous phases are disclosed in U.S. Pat. No. 6,534,456 issued to Hayward et al., on Mar. 18, 2003.

The additional aqueous phase of the present invention may comprise from about 0.1% or from about 0.5% to about 30%, to about 20%, to about 10%, or to about 5%, by weight of the additional aqueous phase, of a water structurant.

The additional aqueous phase of the present invention should be a non-lamellar phase, however, the additional aqueous phase may comprise a lamellar structurant when the phase is also free of titanium dioxide.

Non-limiting examples of inorganic water structurants for use in the personal cleansing composition include silicas, clays such as a synthetic silicates (Laponite XLG™ and Laponite XLS™ from Southern Clay), or mixtures thereof.

Non-limiting examples of charged polymeric water structurants for use in the personal cleansing composition include Acrylates/Vinyl Isodecanoate Crosspolymer (Stabylen 30™ from 3V), Acrylates/Vinyl neodecanoate Crosspolymer (Aculyn 38™ from Rohm and Haas), Acrylates/C10-30 Alkyl Acrylate Crosspolymer (Pemulen TR1™ and TR2™), Carbomers, Ammonium Acryloyldimethyltaurate/VP Copolymer (Aristoflex™ AVC from Clariant), Ammonium Acryloyldimethyltaurate/Beheneth-25 Methacrylate Crosspolymer (Aristoflex HMB™ from Clariant), Acrylates/Ceteth-20 Itaconate Copolymer (Structure 3001™ from National Starch), Polyacrylamide (Sepigel 305™ from SEPPIC), or mixtures thereof.

Non-limiting examples of water soluble polymeric structurants for use in the personal cleansing composition include cellulosic gel, hydroxypropyl starch phosphate (Structure XL™ from National Starch), polyvinyl alcohol, or mixtures thereof.

Non-limiting examples of associative water structurants for use in the personal cleansing composition include synthetic and natural gums and thickeners such as xanthan gum (Ketrol CG-T™ from CP Kelco), succinoglycan (Rheozan™ from Rhodia, gellum gum, pectin, alginates, starches including pregelatinized starches, modified starches, or mixtures thereof.

Non-Migrating Colorant

The multi-phase personal cleansing composition comprises a non-migrating colorant in at least one of the phases of the multi-phase personal cleansing composition. The composition may comprise from about 0.00001%, from about 0.001%, or from about 0.005% to about 10%, to about 1%, to about 0.1%, or to about 0.05%, by weight of the composition of a non-migrating colorant.

To enhance the aesthetic qualities of the present invention, it is important that the non-migrating colorants incorporated into at least one of the phases remain stable and do not migrate from one phase to the other. The Partition Coefficient Values (cLogP) reflect a molecule's hydrophilicity and thus the cLogP calculations are considered for the present invention to determine if they are appropriate to resist migration within the particular phases of the present invention. The cLogP calculations of the present invention reflect the log ratio of the equilibrium concentrations of solute when placed at an n-Octanol (non-polar)-water(polar) system. Hydrophilic colorants are polar which enable them to perform hydrogen bonding and dissolve more readily in water. More hydrophobic colorants, however, favor the n-Octanol phase which effectively increases the cLogP value. Less water soluble colorants also tend to increase the cLogP value due to decreased water solubility. It has been found that colorant materials with a cLogP greater than 2 will resist migration in multi-phase aqueous compositions. Many of these materials with this property are not traditionally used to color personal cleansing compositions and so would not be normally be used by one skilled in the art.

cLogP can be calculated for a variety of commercial compositions with relatively good agreement between the protocols. According to the present invention, the protocol from ACD Labs website was used (www.acdlabs.com). In some cases, where the colorant contains ionizable groups, c Log D (variation of cLogP with pH) can be used at the relevant composition pH.

Accordingly, the non-migrating colorants of the present invention may comprise a cLogP value of at least about 2, at least about 3, at least about 4, or at least about 5. Certain non-migrating colorant materials, however, are effectively insoluble in either phase thus making it difficult to calculate a cLogP value. These non-migrating colorant materials may include, but are not limited to, metal oxides (i.e., iron oxides, titanium dioxide) and micas. Due to their limited water solubility, however, it is understood that the cLogP value will be significantly increased and are considered to have a value greater than about 5 which makes them applicable to the present invention.

While the non-migrating colorants of the present invention may comprise metal ions, i.e. lakes, it is preferred that the non-migrating colorants remain free of barium and aluminum ions to allow for improved lamellar phase stability. The non-migrating colorants may also maintain UV stability.

The non-migrating colorants for use in the multi-phase personal cleansing compositions of the present invention may be selected from the group consisting of organic pigments, inorganic pigments, interference pigments, lakes, natural colorants, pearlescent agents, dyes, carmines, and mixtures thereof.

In the case of lakes, which are colorant materials physi- or chemisorbed onto a substrate (such as talc), the cLogP of the colorant material itself is considered to be the key parameter. For instance, in the table below, the relevant cLogP for D&C Red 30 Talc lake and aluminum lake are identical because it is the cLogP of the Red 30 which is calculated.

Non-limiting examples of non-migrating colorants along with their cLogP values are charted accordingly:

| Colorant | cLogP (www.acdlabs.com) |
|---|---|
| Beta-Carotene | 15.51 |
| D&C Green 6 | 8.35 |
| D&C Red 30 Al Lake | 4.28 |
| D&C Red 30 Talc Lake | 4.28 |
| D&C Red 30 | 4.28 |
| D&C Violet 2 | 7.25 |
| D&C Red 27 Al Lake | 8.76 |
| D&C Red 36 | 5.25 |
| Annatto Extract | 6.32 |
| Titanium Oxide | >5 |

Optional Ingredients

A variety of suitable optional ingredients can be employed in the structured aqueous cleansing phase and the additional aqueous phase. Non-limiting optional ingredients include humectants and solutes. A variety of humectants and solutes may be employed at a level of from about 0.1%, from about 0.5%, or from about 2% to about 50%, to about 35%, or to about 20%, by weight of the personal care composition. Preferred humectants are glycerin, sorbitol and simple and complex sugars.

Suitable optional ingredients further include skin conditioning agents. Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR®

N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR®-205 and Polyox WSR® N-3000 both from Union Carbide); and PEG-90M wherein x equals 2 and n has an average value of about 90,000 (PEG-90M is also known as Polyox WSR®-301 from Union Carbide.)

The multi-phase personal cleansing compositions of the present invention can additionally comprise an organic cationic deposition polymer in the structured aqueous cleansing phase or the additional aqueous phase as a deposition aid. Concentrations of the cationic deposition polymer may range from about 0.025%, from about 0.05%, or from about 0.1% to about 3%, to about 2%, or to about 1%, by weight of the composition.

Suitable cationic deposition polymers for use in the multi-phase personal cleansing composition of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer may be from about 5,000, from about 100,000, or from about 200,000 to about 10 million, to about 2 million, or to about 1.5 million. The polymers also have a cationic charge density ranging from about 0.2 meq/gm, about 0.4 meq/gm, or about 0.6 meq/gm to about 5 meq/gm, at the pH of intended use of the personal cleansing composition, which pH will generally range from about pH 4 or from about pH 5 to about pH 9 or to about pH 8.

Non-limiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10™ which are available from Amerchol Corp. (Edison, N.J., USA) in their Polymer KG, JR and LR series of polymers with the most preferred being KG-30M™.

Other suitable cationic deposition polymers include cationic guar gum derivatives, such as guar hydroxypropyltrimonium chloride, specific examples of which include the Jaguar series (preferably Jaguar C-17™) commercially available from Rhodia Inc., and N-Hance™ polymer series commercially available from Aqualon.

Other suitable cationic deposition polymers include synthetic cationic polymers. The cationic polymers suitable for use in the cleansing composition herein are water soluble or dispersible, non-crosslinked, cationic polymers having a cationic charge density of from about 4 meq/gm or from about 4.2 meq/gm to about 7 meq/gm, to about 6 meq/gm, or to about 5.5 meq/gm. Select polymers should have an average molecular weight of from about 1,000, from about 10,000, or from about 75,000 to about 1 million, to about 500,000, or to about 250,000.

The concentration of the cationic polymer in the cleansing composition may be from about 0.025%, from about 0.1%, or from about 0.2% to about 5%, to about 3%, or to about 1%, by weight of the composition.

A non-limiting example of a commercially available synthetic cationic polymer for use in the cleansing compositions is polymethyacrylamidopropyl trimonium chloride, available under the trade name Polycare 133™, from Rhodia, Cranberry, N.J., U.S.A.

The cationic polymers herein are either soluble in the structured aqueous cleansing phase, or are soluble in a complex coacervate phase in the multi-phase personal cleansing composition formed by the cationic deposition polymer and the anionic surfactant component described hereinbefore. Complex coacervates of the cationic deposition polymer can also be formed with other charged materials in the personal cleansing composition.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid anti Interface Science, Vol. 140, No. 1, November 1990, pp 227-238.

It is believed to be particularly advantageous for the cationic deposition polymer to be present in the personal cleansing composition in a coacervate phase, or to form a coacervate phase upon application or rinsing of the cleansing composition to or from the skin. Complex coacervates are believed to more readily deposit on the skin, which results in improved deposition of the benefit materials. Thus, in general, it is preferred that the cationic deposition polymer exists in the personal cleansing composition as a coacervate phase or forms a coacervate phase upon dilution. If not already a coacervate in the personal cleansing composition, the cationic deposition polymer will preferably exist in a complex coacervate form in the cleansing composition upon dilution with water.

Techniques for analysis of formation of complex coacervates are known in the art. For example, centrifugation analyses of the personal cleansing compositions, at any chosen stage of dilution, can be utilized to identify whether a coacervate phase has formed.

Other non-limiting examples of these optional ingredients include vitamins and derivatives thereof (e.g., ascorbic acid, vitamin E, tocopherol acetate, and the like); sunscreens; thickening agents (e.g., polyol alkoxy ester, available as Crothix from Croda); preservatives for maintaining the antimicrobial integrity of the cleansing compositions (e.g., DMDMH); anti-acne medicaments (resorcinol, salicylic acid, and the like); antioxidants; beads; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), and the like (e.g., clove oil, menthol, camphor, eucalyptus oil, and eugenol). These materials can be used at ranges sufficient to provide the required benefit, as would be obvious to one skilled in the art.

The multi-phase personal cleansing compositions of the present invention can additionally comprise an electrolyte. When present, the electrolyte used in the structured aqueous cleansing phase may be the same as the electrolyte used in the additional aqueous phase. The amount of electrolyte in the individual phases is determined relative to the amount of water. For example for a composition with 2% NaCl and 50% water by weight, the amount of electrolyte may be about 4%. The amount of electrolyte in the structured aqueous cleansing phase may be more than about 0.1%, more than about 0.5% or more than about 1%. When both the structured aqueous cleansing phase and the additional aqueous phase comprise electrolyte, the level of electrolyte in the structured aqueous cleansing phase may be at least about 30%, at least about 40%, at least about 50%, or at least about 75% of the amount of electrolyte added to the additional aqueous phase. The level of electrolyte in the structured aqueous cleansing phase may be less than about 150%, less than about 130%, or less than about 120% of the amount of electrolyte added to the additional aqueous phase.

The structured aqueous cleansing phase of the present compositions can further comprise optional ingredients such as those described hereinafter. Preferred optional ingredients for the structured aqueous cleansing phase include pigments, pH regulators, preservatives or mixtures thereof.

To the extent any optional ingredients described herein include specific materials described hereinbefore as water structurants or lamellar structurants, such materials shall be considered water structurants or lamellar structurants for the purposes of the present invention.

Test Methods
Viscosity Method

The viscosity of the individual phase is determined using a Brookfield DVII+ Pro Viscometer with a helipath attachment using a D spindle at 5 rpm. The sample is loaded into a container with a diameter greater than 2.5" and allowed to equilibrate for at least 12 hours. Prior to reading, the spindle is inserted into the sample to a depth of approximately ¼" and the rotation is begun and the helipath turned on with the direction adjusted to increase the penetration of the spindle into the sample. The viscometer is set up to readout every second, and the first 10 seconds are ignored. The next 5 data points are recorded and averaged to obtain the viscosity.

Lather Volume

Lather volume of a personal care composition can be measured using a graduated cylinder and a tumbling apparatus. A 1,000 ml graduated cylinder is chosen which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal care composition is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. For cleansing applications the personal care compositions may produce a Total Lather Volume of at least about 300 ml or greater than about 600 ml as described in the Lathering Volume Test. The personal care compositions may produce a Flash Lather Volume of at least about 100 ml, greater than about 200 ml, or greater than about 300 ml as described in the Lathering Volume Test.

Method of Use

The multi-phase personal cleansing compositions of the present invention are preferably applied topically to the desired area of the skin or hair in an amount sufficient to provide effective delivery of the skin cleansing agent and skin benefit agents to the applied surface. The compositions can be applied directly to the skin or indirectly via the use of a cleansing puff, washcloth, sponge, or other implement. The compositions are preferably diluted with water prior to, during, or after topical application, and then subsequently rinsed or wiped off of the applied surface, preferably rinsed off of the applied surface using water or a water-insoluble substrate in combination with water.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The multi-phase personal cleansing compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166, U.S. Pat. No. 4,159,028, or US Publication No. 2004/0219119. The method and apparatus allows two or more compositions to be filled with a spiral configuration into a single container. The method requires that at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product.

If the personal cleansing compositions contain stripes of varying colors it can be desirable to package these compositions in a transparent or translucent package such that the consumer can view the pattern through the package. Because of the viscosity of the subject compositions it may also be desirable to include instructions to the consumer to store the package upside down, on its cap to facilitate dispensing.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

Article of Manufacture

The multi-phase personal cleansing compositions of the present invention may be packaged in chemical and physical contact with each other within the same container. Thus, the present invention may also provide for a single chamber package comprising the multi-phase personal cleansing compositions of the present invention. This is advantageous since the compositions can provide for an aesthetically-pleasing pattern visualized through a transparent, single-chamber package. Furthermore, the package of the present invention may comprise a label comprising an ingredient statement comprising the listing of the ingredients that formulate the composition described herein. It is understood that the ingredient label may describe the composition of the present invention in various embodiments.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Each of the prophetic examples below are of personal care compositions comprising 50%, by weight of the personal care composition, of a structured aqueous cleansing phase and 50%, by weight of the personal care composition, of a additional aqueous phase. The amount of each component in a particular phase is provided as a weight percent based on the weight of the particular phase that contains the component.

| Ingredient | Example 1 wt % | Example 2 wt % | Example 3 wt % | Comparative Example 1 wt % |
|---|---|---|---|---|
| I. Lathering Cleansing Phase Composition | | | | |
| Sodium Lauryl Sulfate | | | 7.7 | |
| Sodium Trideceth Sulfate (Cedapol TD-407 ™ from Stepan) | 15.4 | 15.4 | 7.7 | 15.4 |
| Sodium Lauroamphoacetate (Miranol L-32 Ultra ™ from Rhodia) | 4.6 | 4.6 | 4.6 | 4.6 |
| Guar Hydroxypropyltrimonium Chloride (N-Hance 3196 ™ from Aqualon) | 0.7 | 0.7 | 0.6 | 0.7 |
| Xanthan Gum (Keltrol 1000 ™ from Kelco) | 0.6 | 0.6 | 0.5 | 0.6 |
| Isosteareth-2 (Hetoxol IS-2 ™ from Global 7) | 2 | 1 | 2 | 2 |
| Laureth-2 (Arlypon F ™ from | | 2 | | |
| Sodium Chloride | 4.25 | 4.25 | 4.25 | 4.25 |
| Sodium Benzoate | 0.2 | 0.2 | 0.2 | 0.2 |
| Disodium EDTA | 0.13 | 0.13 | 0.13 | 0.13 |
| Glydant | 0.37 | 0.37 | 0.37 | 0.37 |
| Citric Acid | 0.8 | 0.8 | 0.8 | 0.8 |
| Perfume | 2 | 2 | 2 | 2 |
| Water | Q.S. | Q.S. | Q.S. | Q.S. |
| D&C Red 30 Talc Lake (cLogP 4.28) | 0.005 | | | |
| Titanium Dioxide (cLogP >5) | | 0.1 | | |
| D&C Violet 2 (cLogP 7.25) | | | 0.001 | |

| Ingredient | Example 1 wt % | Example 2 wt % | Example 3 wt % | Comparative Example 1 wt % |
|---|---|---|---|---|
| D&C Yellow 5 (cLogP −5.2) | | | | 0.0001 |
| (pH) | (5.7) | (5.7) | (5.7) | (5.7) |
| II. Non-Lathering Structured Aqueous Phase Composition | | | | |
| Acrylates/Vinyl Isodecanoate Crosspolymer (Stabylen 30 ™ from 3V) | 1.0 | 1.0 | 2.0 | 1.0 |
| Xanthan Gum (Keltrol 1000 ™ from Kelco) | 1 | 1 | 1 | 1 |
| D&C Red 30 Talc Lake (cLogP 4.28) | | 0.005 | | |
| Triethanolamine | 0.8 | 0.8 | 1.6 | 0.8 |
| Sodium Chloride | 5 | 5 | 6 | 5 |
| Glydant | 0.37 | 0.37 | 0.37 | 0.37 |
| Colorant | 0.01 | 0.01 | 0.01 | 0.01 |
| Water and Minors | Q.S. | Q.S. | Q.S. | Q.S. |
| (pH) | (5.7) | (5.7) | (5.7) | (5.7) |

The compositions described above can be prepared by conventional formulation and mixing techniques. The structured aqueous cleansing phase can be made by adding the following ingredients into the main mixing vessel in the following sequence: water, sodium lauryl sulfate, sodium trideceth sulfate, sodium lauroamphoacetate sodium chloride, sodium benzoate, disodium EDTA, glydant and salt. Start agitation of the main mixing vessel. In a separate mixing vessel, disperse N-Hance 3196 in water at 1:10 ratio and form a polymer premix. Add the completely dispersed polymer premix into the main mixing vessel with continuous agitation. Disperse the xanthan gum in the isosteareth-2 and then add to the batch. pH adjust with the citric acid, then add the rest of the water, perfume and colorant into the batch. Keep agitation until a homogenous solution forms.

The additional aqueous phase can be prepared by slowly adding Stabylen 30 and xanthan gum into water in a mixing vessel. Then, add salt and neutralize with TEA. Finally, add glydant and colorant with agitation. Mix until homogeneous.

Below are additional prophetic examples of personal care compositions comprising 50%, by weight of the personal care composition, of a structured aqueous cleansing phase and 50%, by weight of the personal care composition, of a additional aqueous phase. The amount of each component in a particular phase is provided as a weight percent based on the weight of the particular phase that contains the component.

| Ingredient | Example 1 wt % | Example 2 wt % |
|---|---|---|
| I. Structured Aqueous Cleansing Phase Composition (Lamellar phase) | | |
| Sodium Lauroamphoacetate | 5.00 | 5.00 |
| Sodium Laureth Sulfate | 10.00 | 10.00 |
| Cocamide MEA | 2.00 | 2.00 |
| Lauric Acid | 2.80 | 2.80 |
| Sunflower Seed Oil | 5.00 | 5.00 |
| Crodalan LA | 1.00 | 1.00 |
| Glycerin | 2.00 | 2.00 |
| Guar Hydroxypropyltrimonium Chloride | 0.50 | 0.50 |
| Citric Acid | 1.00 | 1.00 |
| DMDM Hydantoin + Iodopropynyl Butylcarbamate | 0.22 | 0.22 |
| D&C Red 27 (cLogP 8.76) | 0.001 | 0.001 |
| EDTA | 0.02 | 0.02 |
| EHDP (Etidronic Acid) | 0.02 | 0.02 |
| Perfume | 1.00 | 1.00 |
| Water | Q.S. | Q.S. |
| II. Additional Aqueous Phase Composition (Isotropic phase) | | |
| Sodium Laureth Sulfate | 11.00 | 11.00 |
| Cocamidopropyl Betaine | 3.00 | 3.00 |
| Dimethicone Copolyol Sulfosuccinate | 0.50 | |
| Hydroxypropyl Guar Hydroxypropyltrimonium Chloride | 0.10 | |
| Propylene Glycol | 0.50 | |
| Acrylates Copolymer (suspension) | 3.00 | |
| Acrylates/Steareth-20 methacrylate copolymer | 0.50 | |
| Acrylates/C12-24 Acrylate Copolymer | | 0.50 |
| DMDM Hydantoin + Iodopropyl Butylcarbamate | 0.22 | 0.22 |
| Sodium Hydroxide | 0.60 | 0.60 |
| Water | Q.S. | Q.S. |

The compositions described above can be prepared by conventional formulation and mixing techniques.

Below are additional prophetic examples of personal care compositions comprising 50%, by weight of the personal care composition, of a structured aqueous cleansing phase and 50%, by weight of the personal care composition, of a additional aqueous phase. The amount of each component in a particular phase is provided as a weight percent based on the weight of the particular phase that contains the component.

| Ingredient | Example 1 wt % | Example 2 wt % | Example 1 wt % | Example 2 wt % |
| --- | --- | --- | --- | --- |
| I. Structured Aqueous Cleansing Phase Composition (Lamellar phase) | | | | |
| Sodium Lauroamphoacetate | 3.00 | 18.00 | 12.00 | 4.00 |
| Sodium Laureth Sulfate | 6.00 | 5.00 | 9.00 | |
| Ammonium Laureth Sulfate | | | | 3.00 |
| Ammonium Lauryl Sulfate | | | | 4.00 |
| Cetyl Actetate and Acetylated Lanolin Alcohol | 1.50 | | 1.00 | |
| Petrolatum | | | | 15.00 |
| Lauric Acid | 2.50-3.20* | 1.60 | 3.40 | 3.20 |
| Sunflower Seed Oil | 8.00 | 10.00 | 10.00 | |
| Cocamide MEA | 2.00 | 2.50 | 2.00 | 2.00 |
| Glycerin | 2.00 | 2.00 | 6.00 | 8.00 |
| Guar Hydroxypropyltrimonium Chloride | 0.50 | 0.50 | 1.00 | 1.00 |
| Citric Acid | 0.70 | 1.00 | 0.80 | 0.90 |
| DMDM Hydantoin + Iodopropynyl Butylcarbamate | 0.20 | 0.20 | 0.20 | 0.20 |
| D&C Green 6 (cLogP 8.35) | 0.001 | 0.001 | 0.001 | 0.001 |
| Vitamin E Acetate | 0.10 | 0.20 | | 0.20 |
| Vitamin A Palmitate | | | 0.20 | |
| EDTA | 0.02 | 0.02 | 0.02 | 0.02 |
| EHDP (Etidronic Acid) | 0.02 | 0.02 | 0.02 | 0.02 |
| Perfume | 0.50 | 1.50 | 1.00 | 1.40 |
| Water | Q.S. | Q.S. | Q.S. | Q.S. |
| II. Additional Aqueous Phase Composition (Lamellar phase) | | | | |
| Sodium Lauroamphoacetate | 7.00 | 10.00 | 5.00 | 10.00 |
| Sodium Laureth Sulfate | 14.00 | 15.00 | 15.00 | 7.00 |
| Sodium Lauroyl Sacosinate | | | 4.00 | |
| Sodium Lauryl Sulfate | | | | 3.00 |
| Cetyl Actetate and Acetylated Lanolin Alcohol | 0.50 | | 0.50 | |
| Isostearic Acid | | | | 3.50 |
| Beads | | 1.00 | | |
| Lauric Acid | 2.50-3.00* | 1.20 | 3.60 | |
| Sunflower Seed Oil | 3.00 | 10.00 | | 5.00 |
| Cocamide MEA | 2.00 | 2.50 | 2.00 | 2.00 |
| Glycerin | 2.00 | | 4.00 | 7.00 |
| Guar Hydroxypropyltrimonium Chloride | 0.50 | 0.50 | 0.50 | 0.60 |
| Citric Acid | 1.20 | 0.50 | 0.70 | 0.90 |
| DMDM Hydantoin + Iodopropynyl Butylcarbamate | 0.20 | 0.20 | 0.20 | 0.20 |
| EDTA | 0.02 | 0.02 | 0.02 | 0.02 |
| EHDP (Etidronic Acid) | 0.02 | 0.02 | 0.02 | 0.05 |
| Triclosan | | | | 0.50 |
| Perfume | 0.50 | 1.00 | 0.50 | 0.60 |
| Water | Q.S. | Q.S. | Q.S. | Q.S. |

*to adjust viscosity

The structured aqueous cleansing phase and additional aqueous phase exemplified above may be combined in a transparent package according to the process described in US 2004/0219119 to form a multi-phase personal cleansing composition of the present invention.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of stabilizing colorant in a multi-phase aqueous personal care composition, comprising:
    identifying a colorant as a non-migrating colorant, wherein said colorant has a cLogP value of about 2 or greater; and
    formulating with said non-migrating colorant in the multi-phase personal cleansing composition comprising:
    a) a structured aqueous cleansing phase comprising a surfactant and water; and
    b) at least one additional, non-lamellar aqueous phase;
    wherein at least one of said structured aqueous cleansing phase and said additional aqueous phase comprises at least one of the non-migrating colorant; and
    wherein said structured aqueous cleansing phase and said additional phase are packaged in physical contact with one another.

2. The method of claim 1, wherein said non-migrating colorant is substantially free of metals selected from the group consisting of Barium, Aluminum, and mixtures thereof.

3. The method of claim 1, wherein said non-migrating colorant is selected from the group consisting of organic pigments, inorganic pigments, interference pigments, lakes, natural colorants, pearlescent agents, dyes, carmines, and mixtures thereof.

4. The method of claim 1, wherein said structured aqueous cleansing phase is a lamellar phase and said additional aqueous phase is an isotropic phase.

5. The method of claim 1, wherein the additional aqueous phase is substantially free of surfactant.

6. The method of claim 1, wherein the composition comprises from about 0.00001% to about 10%, by weight of the composition, of said non-migrating colorant.

7. The method of claim 1, wherein said non-migrating colorant is UV stable.

8. The method of claim 4, wherein said lamellar phase comprises a lamellar structurant selected from the group consisting of fatty acids and derivatives thereof, fatter esters and derivatives thereof, fatty alcohols and derivatives thereof, trihydroxystearin, and mixtures thereof.

9. The method of claim 8, wherein said fatty acids are selected from the group consisting of lauric acid, oleic acid, isostearic acid, linoleic acid, linolenic acid, ricinoleic acid, elaidic acid, arichidonic acid, myristoleic acid, palmitoleic acid, and mixtures thereof.

10. The method of claim 9, wherein the composition has a viscosity of from about 3,000 cps to about 1,000,000 cps.

11. The method of claim 9, wherein the structured aqueous has a lather volume of at least about 500 mL.

12. The method of 9, wherein the additional aqueous phase is substantially free of surfactant.

13. The method of claim 9, wherein the non-migrating colorant is free of titanium dioxide.

* * * * *